United States Patent
Eichler

(10) Patent No.: US 7,532,921 B2
(45) Date of Patent: May 12, 2009

(54) MEASURING ELECTRODE SYSTEM

(76) Inventor: Ruediger Eichler, Tiefenbacherstrasse 5, 97225 Zellingen (DE)

(*) Notice: Subject to any disclaimer, the term of this patent is extended or adjusted under 35 U.S.C. 154(b) by 144 days.

(21) Appl. No.: 10/525,054

(22) PCT Filed: Aug. 20, 2003

(86) PCT No.: PCT/EP03/09228

§ 371 (c)(1),
(2), (4) Date: Aug. 9, 2005

(87) PCT Pub. No.: WO2004/017829

PCT Pub. Date: Mar. 4, 2004

(65) Prior Publication Data

US 2006/0155181 A1  Jul. 13, 2006

(30) Foreign Application Priority Data

| Aug. 21, 2002 | (DE) | ................................. 102 38 310 |
| Nov. 26, 2002 | (EP) | .................. PCT/EP2002/13327 |
| Jan. 15, 2003 | (DE) | ................................. 103 01 258 |

(51) Int. Cl.
*A61B 5/04* (2006.01)

(52) U.S. Cl. ........................ 600/372; 600/397

(58) Field of Classification Search ................ 600/372, 600/382–393, 397–399; 607/153
See application file for complete search history.

(56) References Cited

U.S. PATENT DOCUMENTS

| 2,895,479 | A | * | 7/1959 | Lloyd ............................ 600/384 |
| 3,580,239 | A | * | 5/1971 | Wantanabe et al. .......... 600/361 |
| 3,590,810 | A | * | 7/1971 | Kopecky ....................... 600/396 |
| 3,788,317 | A | | 1/1974 | McCormick |
| 3,942,517 | A | * | 3/1976 | Bowles et al. ................ 600/392 |
| 3,993,048 | A | * | 11/1976 | Francis ........................ 600/395 |
| 4,220,159 | A | * | 9/1980 | Francis et al. ............... 600/395 |
| 4,362,165 | A | * | 12/1982 | Carmon et al. .............. 600/396 |
| 4,559,950 | A | * | 12/1985 | Vaughan et al. ............. 600/394 |
| 4,763,660 | A | * | 8/1988 | Kroll et al. .................. 600/391 |
| 4,842,577 | A | | 6/1989 | Konno et al. |
| 5,341,806 | A | * | 8/1994 | Gadsby et al. .............. 600/393 |
| 5,362,308 | A | | 11/1994 | Chien et al. |
| 5,496,266 | A | | 3/1996 | Haak et al. |
| 5,582,587 | A | * | 12/1996 | Gyory et al. .................. 604/20 |
| 5,810,742 | A | | 9/1998 | Pearlman |
| 6,301,493 | B1 | * | 10/2001 | Marro et al. ................ 600/383 |
| 6,488,428 | B1 | * | 12/2002 | Fischer ........................ 401/133 |
| 6,526,303 | B1 | * | 2/2003 | Scampini .................... 600/391 |

FOREIGN PATENT DOCUMENTS

| EP | 0 571 712 A2 | 12/1993 |
| GB | 2 359 995 A | 9/2001 |

* cited by examiner

*Primary Examiner*—Lee S Cohen
*Assistant Examiner*—Victoria W Chen
(74) *Attorney, Agent, or Firm*—Gallagher & Kennedy, P.; Thomas D. MacBlain

(57) ABSTRACT

This invention relates to a measuring electrode arrangement (1), in particular for electroimpedance tomography, having at least one measurement object (5) for electric motor contacting of a measurement object (2). It is proposed that a storage space (7) which contains a contact medium (6) for reducing the electric contact resistance between the measuring electrode (5) and the measurement object (2) is located on the side of the measuring electrode (5) facing away from the measurement object (2), said storage space containing a contact medium (6) for reducing the electric contact resistance between the measuring electrode (5) being at least partially permeable for the contact medium (6).

13 Claims, 2 Drawing Sheets ponents of the contact medium. For example, the contact medium may contain ions in aqueous solution, these ions being able to penetrate through the measuring electrode, whereas the liquid used as the solvent is retained in the storage space.

MEASURING ELECTRODE SYSTEM

FIELD OF THE INVENTION

This invention relates to a measuring electrode arrangement, in particular for electroimpedance tomography.

BACKGROUND OF THE INVENTION

To perform so-called electroimpedance tomography (EIT) on a patient, several measuring electrodes must be attached to the patient's body part that is to be examined, e.g., the patient's chest. The measuring electrodes must be positioned as accurately as possible here and their positions must be maintained with the greatest possible accuracy during the measurement process, because improper positioning of the measuring electrodes would distort the result of the measurement. In addition, the measuring electrodes must make electric contact as well as possible with the part of the body to be examined, i.e., the contact resistance between the measuring electrodes and the parts of the body to be examined should be as low as possible and must not fluctuate during the measurement process.

Therefore, measuring electrode arrangements for electroimpedance tomography are known in which multiple electrodes are attached to the body surface of the patient, thus preventing a change in the electrode potential during the measuring process. The electric contacting of the patient's body part to be tested may, however, change during the measuring process or between several successive measurement operations if a contact fluid provided between the attached electrode and the body surface dries out. One disadvantage of the known measuring electrode arrangements for electroimpedance tomography is therefore the unsatisfactory electric contacting of the measurement object.

SUMMARY OF THE INVENTION

The object of this invention is therefore to create a measuring electrode arrangement that is especially suitable for electroimpedance tomography and permits the best possible electric contacting of the measurement object.

This invention includes the general technical teaching of integrating a supply space for a contact medium into the measuring electrode arrangement, whereby the contact medium reduces the electric contact resistance between the measuring electrode and the object of measurement.

The supply space for the contact medium is preferably located on the side of the measuring electrode that faces away from the measurement object, whereby the measuring electrode is at least partially permeable for the contact medium so that the contact medium can penetrate out of the storage space into the space between the surface of the measurement object and the measuring electrode.

The contact medium for reducing the electric contact resistance may be a liquid, a gel, a foam or a paste. However, this invention is not limited to these types of contact media but instead can also be implemented with other substances which contribute to a reduction in the electric contact resistance between the measuring electrode and the measurement object. The measuring electrode may be permeable for the contact medium with all its ingredients, so that, for example, a fluid used as a contact medium can penetrate through the measuring electrode. As an alternative, however, it is also possible for the measuring electrode to be permeable only for individual components of the contact medium, whereas the measuring electrode is impermeable for the remaining components of the contact medium. For example, the contact medium may contain ions in aqueous solution, these ions being able to penetrate through the measuring electrode, whereas the liquid used as the solvent is retained in the storage space.

The measuring electrode arrangement according to this invention is preferably attached to the object to be measured by gluing. An adhesive layer is preferably arranged for this purpose on the side of the measuring electrode arrangement facing the measurement object in order to attach the measuring electrode arrangement to the measurement object. However, this invention is not limited to this type of attachment of the measuring electrode arrangement to the measurement object. Instead there are also many other possibilities for mechanical fixation of the measuring electrode arrangement on the measurement object, e.g., by means of a belt-like electrode carrier which is placed around the patient's chest and secures the individual measuring electrodes in a predetermined geometric configuration. The supply space for the contact medium is preferably bordered by a plastic layer, which is preferably arranged on the side of the measuring electrode facing away from the measurement object. Such a plastic layer may consist of polyethylene (PE), for example, but other materials are also possible. The plastic layer which serves as the border of the storage space with respect to the measuring electrode is preferably attached by heat welding or ultrasonic welding, but other manufacturing methods are also conceivable.

In addition, the inventive measuring electrode arrangement has at least one electric shield, which consists of an electrically conductive material and is electrically insulated with respect to the measuring electrode. When the inventive measurement electrode arrangement is used as a stimulation electrode in performing electroimpedance tomography, such an electric shield serves to shield the measuring electrodes in the environment from the interference field caused by the stimulation. When using the measuring electrode arrangement according to this invention to detect the potential distributions that occur as part of electroimpedance tomography, however, the shield serves to shield the interfering fields induced by stimulation electrodes that might be nearby.

In one embodiment, the inventive measuring electrode arrangement has multiple measuring electrodes which are electrically insulated from one another and thereby permit separate measurement and/or stimulation.

Multiple electric shields are preferably provided here and are electrically insulated with respect to one another and the individual measuring electrodes. Such an arrangement with multiple separate electric shields offers the possibility of having an electric signal act on the shields to improve the shielding effect. With use of a measuring electrode as a stimulation electrode, the respective shield may be acted upon by an electric signal in a targeted way, said signal compensating for the interfering field caused by the stimulation.

However, as an alternative, it is also possible for the electric measuring electrode arrangement to have a common electric shield for all the measuring electrodes, whereby the common shield is preferably being applied to ground potential.

In the inventive measuring electrode arrangement, the shield is preferably arranged on the side of the measuring electrode facing away from the measurement object in order to achieve the best possible shielding effect.

In a preferred exemplary embodiment, the individual measuring electrodes are arranged on a belt-shaped electrode carrier, whereby the electrode carrier is stretchable for adjusting the electrode spacing. Finally, this invention also includes the use of the inventive measuring electrode arrangement in electroimpedance tomography.

The measurement object to be tested here is preferably a patient's chest, with the inventive measuring electrode arrangement being attached to the chest so that electroimpedance tomography can be performed. However, this invention is not limited to a patient's chest with regard to the measurement object to be tested but instead may also fundamentally be used with other body parts.

Other advantageous refinements of this invention are characterized in the subclaims and are explained below in greater detail in the description of a preferred exemplary embodiment of this invention.

DETAILED DESCRIPTION OF THE PREFERRED EMBODIMENTS

Figure 1:
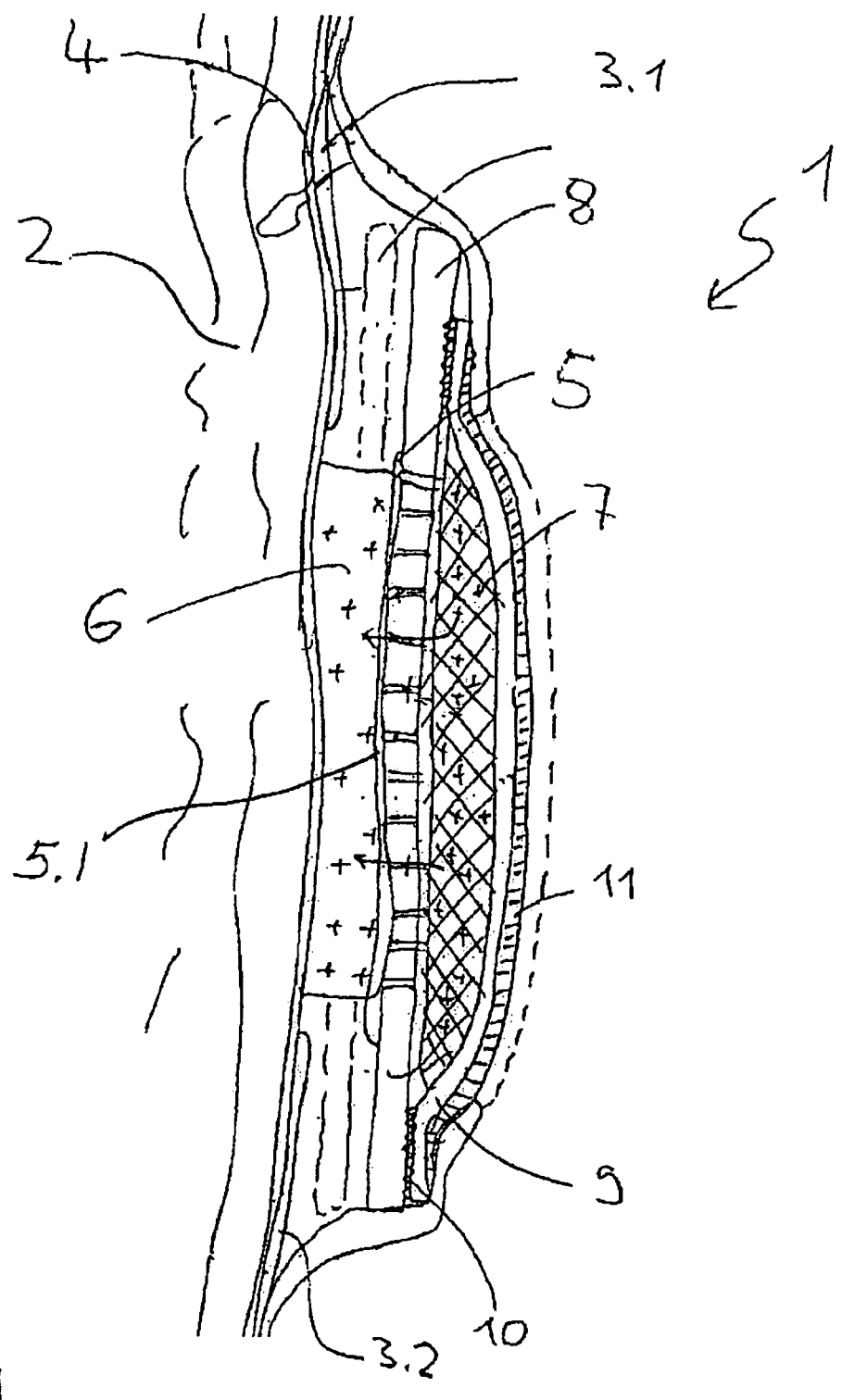
FIG. 1 shows a cross-sectional view of an inventive electrode arrangement.
Figure 2:
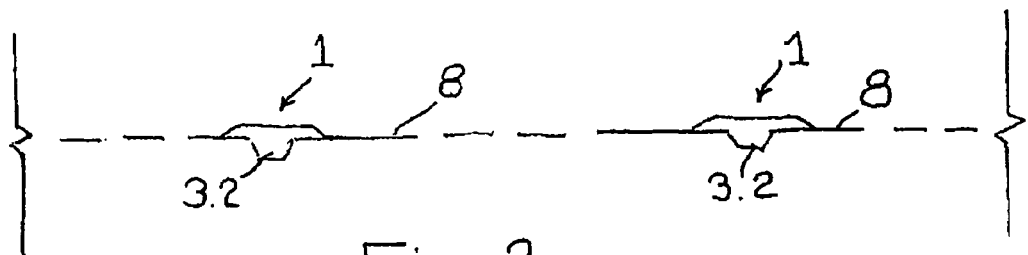
FIG. 2 is a schematic illustration of an embodiment of the invention of FIG. 1 and shows multiple electrode arrangements on a belt-like carrier.

The measuring electrode arrangement 1 shown in FIG. 1 is used for electric contacting of a patient's chest 2 in electroimpedance tomography.

The electrode arrangement is currently designed in the form of a belt which is placed around the patient's chest 2 and attached to the patient's skin surface 4 by two strips of adhesive tape 3.1, 3.2. This mechanical attachment of the electrode arrangement on the body surface 4 prevents the placement of the measuring electrode arrangement 1 during one electroimpedance tomography procedure or between multiple successive tomography procedures from changing, which would distort the measurement result.

Several measuring electrodes are distributed over the circumference of the patient's chest 2 in the measuring electrode arrangement 1, but only one measuring electrode 5 is depicted in the cross-sectional view. The measuring electrode 5 here is not in direct contact with the body surface 4 but instead is arranged at a distance from the body surface 4. In electroimpedance tomography, the space between the measuring electrode 5 and the body surface 4 is filled by an electrically conductive gel 6 which contains ions and therefore causes a good electric contact with the body surface 4.

When a measurement procedure lasts a long time or when there are prolonged pauses between successive measurement procedures, there is the risk that the gel 6 in the space between the electrode 5 and the body surface 4 might dry out, which would have a deleterious effect on the electric contact. The measuring arrangement 1 according to this invention therefore has a storage space 7 containing an electrically conducting gel on the side of the measuring electrode 5 facing away from the chest. As shown in FIG. 1, the electrode 5 defines an imperforate region 5.1 of the electrode that separates the storage space 7 from the area of contact where the measurement object is contacted by the contact medium. The ions in the storage space 7 in the gel 6 can then diffuse through the measuring electrode 5 into the space between the measuring electrode 5 and the body surface 4 to keep the conductivity of the gel 6 and thus the electric contact with the body surface 4 at the most constant possible level. The measuring electrode 5 is therefore permeable for the ions in the gel 6, whereas the measuring electrode 5 is otherwise impermeable for the gel 6.

In addition, the inventive measuring electrode arrangement 1 has an electrode carrier 8 to which a plastic layer 9 is attached on the side facing away from the chest 2, with the plastic layer 9 bordering the storage space 7. The plastic layer 9 is attached to the electrode carrier 8 here by thermal welding 10.

Figure 3:
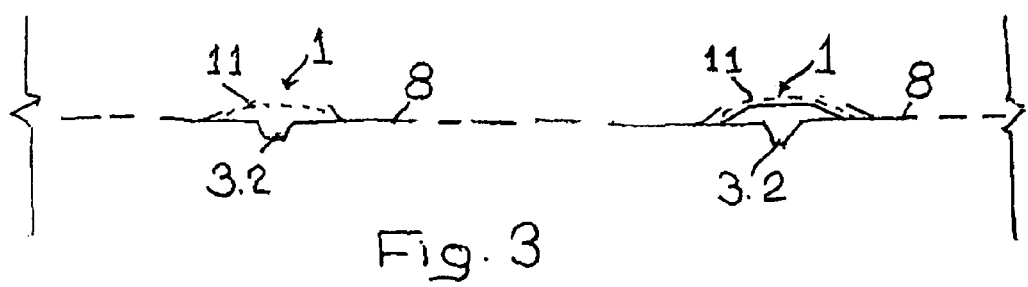
FIG. 3 is another schematic illustration like that of FIG. 2 and further shows electric shields shielding the multiple electrode arrangements.
Figure 4:
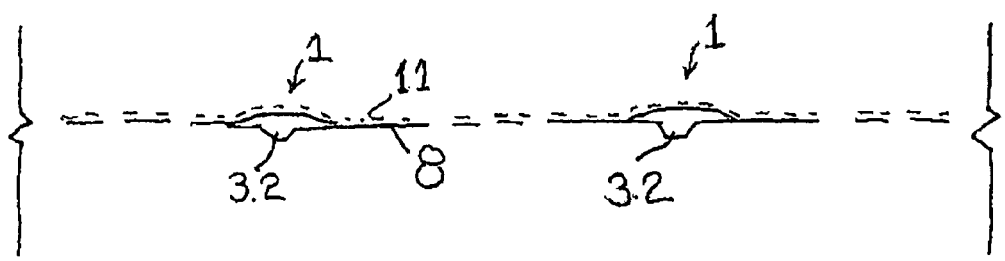
FIG. 4 is a further schematic illustration and further shows a common electric shield shared among the several electrode arrangements.

Finally, the measuring electrode arrangement 1 according to this invention also has an electric shield 11 which is applied to the side of the plastic layer 9 facing away from the storage space 7 and consists of an electrically conductive material. Schematically illustrated in FIG. 3, a shield 11 is provided for each of the measuring electrodes 5 distributed over the circumference of the patient's chest 2, the individual shields 11 being electrically insulated with respect to one another and with respect to the measuring electrode 5. The individual shields 11 may therefore be acted upon by an electric signal in a controlled manner to provide shielding from interfering fields. However, it also possible to simply connect the individual shields 11 to ground. In addition, as shown schematically in FIG. 4, the measuring electrode arrangements 1 may have a common electric shield 11.1.

This invention is not limited to the exemplary embodiment described above. Instead, a plurality of variants and modifications are possible, also making use of the inventive idea and therefore falling within the scope of patent protection.

The invention claimed is:

1. A measuring electrode arrangement for electroimpedance tomography, comprising:
    at least one measuring electrode for electrically connecting to a measurement object through a contact medium, said measuring electrode being arranged at a distance from an area of contact at which a surface location of the measurement object is to be contacted by the contact medium;
    a space located between the measuring electrode and the area of contact, said space being filled with the contact medium;
    a storage space located on the side of the measuring electrode facing away from the area of contact, the storage space containing a contact medium for reducing the electric contact resistance between the measuring electrode and the measurement object, the measuring electrode being at least partially permeable for the contact medium in the storage space, the contact medium in the storage space containing ions in a solvent in solution, and wherein the ions can penetrate through the measuring electrode, and the measuring electrode is impermeable for the solvent.

2. The measuring electrode arrangement according to claim 1, wherein the solvent of the contact medium is a liquid, a gel, a foam or a paste.

3. The measuring electrode arrangement according to claim 1, wherein an adhesive layer is arranged on at least one surface of the measuring electrode arrangement in order to attach the measuring electrode arrangement to the measurement object.

4. The measuring electrode arrangement according to claim 1, wherein the storage space is bordered by a plastic layer.

5. The measuring electrode arrangement according to claim 1, further comprising at least one electric shield which comprises an electrically conductive material and is electrically insulated with respect to the measuring electrode.

6. The measuring electrode arrangement according to claim 5, further comprising a plurality of measuring electrodes that are electrically insulated with respect to one another.

7. The measuring electrode arrangement according to claim 6, further comprising a plurality of shields that are electrically insulated with respect to one another, each shield being arranged on one of the measuring electrodes.

8. The measuring electrode arrangement according to claim 6, further comprising a common electric shield for the measuring electrodes.

9. The measuring electrode arrangement according to claim 5, wherein the shield is located on the side of the measuring electrode facing away from the area of contact.

10. The measuring electrode arrangement according to claim 6, wherein the measuring electrodes are mounted on a belt-like electrode carrier, wherein the electrode carrier is extensible for adjusting the electrode spacing.

11. The measuring electrode arrangement according to claim 1, wherein the at least partially permeable measuring electrode is imperforate in a region extending across the storage space.

12. In a method of electroimpedence tomography, the improvement comprising:
 (a) providing a measuring electrode arrangement according to any one of claims 1-10,
 (b) securing the measuring electrode to the measurement object, and
 (c) applying an electrical impulse to the measurement object.

13. A measuring electrode arrangement for electroimpedance tomography, including at least one measuring electrode for electrically connecting to a measurement object through a contact medium at an area of contact, a storage space arranged on the side of the measuring electrode facing away from the area of contact on the opposite side of the measuring electrode from the area of contact so that the measuring electrode separates the storage space from the area of contact at which a measurement object is to be contacted, the storage space containing a contact medium for reducing the electric contact resistance between the measuring electrode and the measurement object, the measuring electrode being at least partially permeable for the contact medium contained in the storage space so as to assure continuing reduced resistance electrical contact between the measuring electrode and the measurement object through the contact medium.

* * * * *